US005626562A

United States Patent [19]
Castro

[11] Patent Number: 5,626,562
[45] Date of Patent: May 6, 1997

[54] DRUG DELIVERY CATHETER

[75] Inventor: Anthony J. Castro, San Francisco, Calif.

[73] Assignee: Devices for Vascular Intervention, Santa Clara, Calif.

[21] Appl. No.: 345,104

[22] Filed: Nov. 28, 1994

[51] Int. Cl.$^6$ ............................................. A61M 31/00
[52] U.S. Cl. ........................ 604/53; 606/159; 606/180
[58] Field of Search ........................... 604/51–55, 22, 604/96, 891.1; 606/159, 170, 171, 180

[56] References Cited

U.S. PATENT DOCUMENTS

| | | | |
|---|---|---|---|
| 4,795,427 | 1/1989 | Helzel | 604/53 |
| 4,846,192 | 7/1989 | MacDonald | 604/22 |
| 5,087,244 | 2/1992 | Wolinsky et al. | 604/96 |
| 5,279,565 | 1/1994 | Klein et al. | 604/53 |
| 5,431,673 | 7/1995 | Summers et al. | 606/170 |

*Primary Examiner*—John D. Yasko
*Attorney, Agent, or Firm*—Anthony J. Castro, Esq.; Douglas A. Chaikin, Esq.; Peninsula IP Group

[57] ABSTRACT

A device and method for the localized treatment of vasculature with drugs and medicaments is described herein. Centrifugal force is used to drive a material from a reservoir to the outer surface of the application device and thereby deliver the treatment substance to the chosen area.

24 Claims, 3 Drawing Sheets

DRUG DELIVERY CATHETER

RELATED APPLICATIONS

This application incorporates by reference U.S. patent application Ser. No. 08/149,587, filed Nov. 11, 1993, entitled "Improved Cutter Device," and Ser. No. {08/597,603,}filed Feb. 6, 1996, entitled "Composite Cutter."

BACKGROUND OF THE INVENTION

1. Field of the Invention

This invention relates to a device and method for the treatment of specific areas of inner surfaces of biological conduits with medicaments.

2. Previous Art

Atherosclerosis is a progressive disease wherein fatty, fibrous, calcific, or thrombotic deposits produce atheromatous plaques within and beneath the intima which is the innermost layer of arteries. The most commonly affected vessels are the aorta, iliac, femoral, coronary and cerebral arteries. Untreated coronary artery disease can lead to angina, hypertension, myocardial infection, strokes and the like. Atherosclerotic blockages can occur anywhere within the thicket of vessels and arteries that service the heart. Regions of blood vessels that are blocked by atheroma (plaque) or other materials are generally referred to herein as stenotic regions, and the blocking material as stenotic material. The composition of the stenotic material can vary from hard calcium-containing lesions to fatty lipid-based coatings on the inside of the coronary arteries. Stenotic materials deposited on blood vessel walls are often relatively soft and tractable. However, in many cases, the stenotic material may contain a significant amount of calcified and hardened material. A number of methods such as coronary artery bypass graft (CABG) surgery, percutaneous transluminal coronary angioplasty, (PCTA), direction coronary atherectomy (DCA), energetic ablation, and stenting, are used in attempts to restore the narrowed blood vessels to, as close as is possible, to their original diameters. In percutaneous transluminal coronary angioplasty, sometimes called balloon angioplasty, during coronary catheterization, an inflatable balloon is inserted in a coronary artery in the region of coronary stenosis. Inflation of the balloon for 15-30 seconds results in an expansion of the narrowed lumen or passageway. Devices suitable for PCTA have been described is U.S. patents such as U.S. Pat. No. 4,323,071. Directional Coronary Atherectomy is a procedure which has been developed for excising and removing stenotic material from the vascular system. DCA procedures employ a variety of special catheters having tissue cutting members (cutters) located at the distal end of the catheter. In use, the catheter is inserted into a biological conduit so that the cutter housing is placed adjacent to the stenotic region with the housing window aligned to the stenotic material. Stenotic material is invaginated into an opening in the cutter housing by inflating a balloon opposed to the housing window. Simultaneous rotation and translation of the cutter sever the stenotic material which is retained in the nosecone at the distal end of the catheter. Examples of such devices can be found in U.S. Pat. Nos. 5,312,425; 5,250,959; 5,181,920; 5,071,425; 4,979,951; 4,781,186; and 4,669,469 (reissued as No. Re. 33,569), herein incorporated by reference in their entirety. Ablative methods such as the application of laser energy to the atheroma or high speed abrasive burrs are also used to widen the blood vessel at the point of stenosis. Another method of treatment of cardiac insufficiency employs stents, (mechanical supports). Stents are placed at the site of the stenosis and expanded to widen the blood vessel. The stent remains in place as an arterial implant. All of these techniques are used to open blocked areas of blood vessels in an attempt to restore the original lumen diameter or provide an alterative path for blood flow. Although these methods of treatment are distinct different methods, they share one common problem, restenosis. A certain percentage of the treated blood vessels will reocclude (restenose) after a period of time. Restenosis can occur in as many as 30-40% of the cases. In such restenotic instances, the original procedure may be repeated or an alternative method for achieving blood flow may be tried. The common factor in all of these treatment methods is that they all traumatize the blood vessel to some extent. There are several reasons why restenosis can occur. One is that small clots form on the arterial wall. Tears in the wall expose blood to foreign material and proteins, such as collagen, which are highly thrombogenic. Resulting clots can grow gradually, or can contain growth hormones which are released by platelet within the clot. Additionally, growth hormones released by other cells, such as macrophages, can cause smooth muscle cells and fibroblasts in the region to multiply. Further, there is often complete loss of the normal single layer of cells constituting the endothelial lining following angioplasty. This layer normally covers the internal surface of all vessels, rendering that surface compatible, i.e., non-thrombogenic and non-reactive with blood. Mechanically, when as angioplasty balloon is inflated, the endothelial cells are torn away. Prior art procedures also produce injuries in the arterial wall which become associated with inflammation. Any kind of inflammatory response may cause the growth of new tissue. In order to address such problems, the cardiology community needs to administer drugs which are biocompatible and in such concentration that they do not induce a toxic reaction.

Some drugs might have a beneficial effect upon inhibition of the stenotic growth or even remove the stenotic material but, treatment of the site of vessel blockage via systemic administration of drugs has not been successful. The area in need of treatment is very small relative to the area of the vascular system. Blood flow at the stenotic region is low and variable. Localized application of some drugs could achieve the most effective result without burdening the entire system with large amounts of a drug. One attempt to localize drug delivery during an angioplasty procedure is described in U.S. Pat. No. 5,199,951. This patent is limited in the area of treatment, and method of application. There does not exist an efficient means for the localized delivery of medicaments in a biological conduit such as a blood vessel.

What is needed is a method of applying a medicant to a specific site in a biological conduit to either remove or destroy the stenotic material or to treat the site of vascular intervention to prevent restenosis.

SUMMARY OF THE INVENTION

It is an object of this invention to provide a device and method for applying medicaments to a biological conduit.

In accordance with the above object and those that will be mentioned and will be apparent below, a device for applying medicaments to a biological conduit is provided comprising:
a rotatable and axially translatable applicator that is further comprised of
an outer surface;
a distal end;
an interior reservoir;
a drug contained in said reservoir;

at least one delivery path connecting the interior reservoir to the surface of the said applicator; and a drive cable attached to the proximal end of said applicator for imparting rotational and translational motion to said applicator, whereby the medicament contained in said reservoir is delivered said biological conduit when the applicator is rotated.

In the event that a drug is applied that is effective for removing or otherwise controlling the stenotic material without need of excising or compressing stenotic material, the housing window can be optimized to the extent required to maintain structural rigidity and permit the largest area of application.

BRIEF DESCRIPTION OF THE DRAWINGS

For a further understanding of the objects and advantages of the present invention, reference should be had to the following detailed description, taken in conjunction with the accompanying drawing, in which like parts are given like reference numerals and wherein.

DETAILED DESCRIPTION OF THE INVENTION

Figure 1:
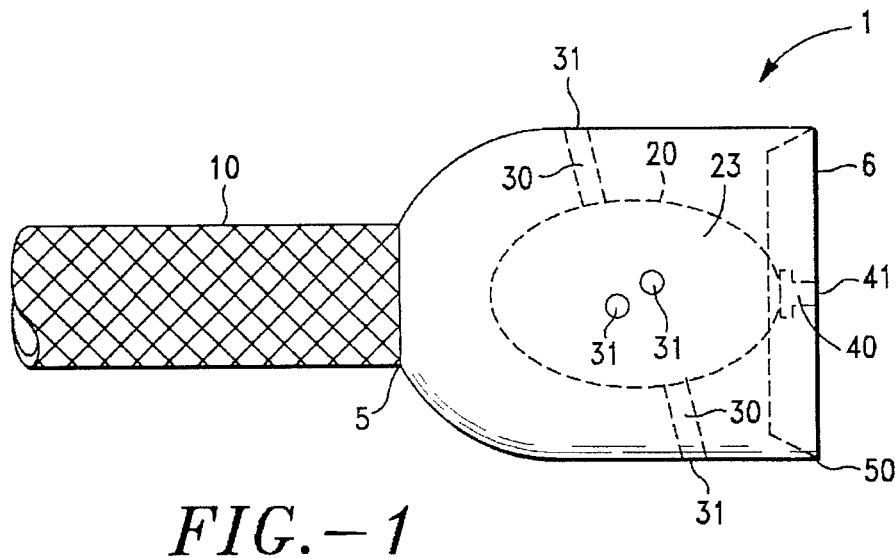
FIG. 1 is a side view of an cutting applicator in accordance with the present invention.

With respect to FIG. 1 is shown a medicament applicator 1 having a proximal end 5, a distal end 6, a medicament reservoir 20, delivery paths 31), openings to the exterior 31, a sealing plug 40 and a cutting edge 50. The applicator 1 is attached to a drive cable 10 at proximal end 5 which is attached to a motor drive (not shown). Reservoir 20 contains a porous absorbent material 23, such as cotton, open celled cellulosic foam, open celled polyurethane foam or the like. The drug to be delivered can be loaded through port 41 into reservoir 20 and absorbed by absorbent material 23 when the device is manufactured and sealed in place by plug 40 or injected by means of a hypodermic syringe and needle into reservoir 20 through plug 40 just prior to use. Drugs that have sufficient storage stability may lend themselves to the preloading approach. Drugs that have a limited lifetime can be prepared just prior to the treatment and injected into the reservoir 20 through sealing plug 40. In a preferred embodiment, the reservoir 20 contains an absorbent material 23 that will retain the absorbed drug by absorption until the applicator 1 is rotated above a threshold high speeds. Thus, the cutting applicator 1 is first rotated and translated axially to remove the stenotic material. Then, when the application of drug is desired, the cutting applicator 1 is rotated an a higher speed that is sufficient to express out the drag of reservoir 20 via path 30 to opening 31. In this manner, several cuts may be made in various positions, and drug may be applied to each cut after it is made. In the embodiment shown in FIG. 1, the drug delivery paths 30, are at an angle to the perpendicular of the axis of rotation of the applicator 1 and permit treatment a larger area of blood vessel that would be possible if the openings were perpendicular from the axis of rotation and equidistant from a central point. In this manner, one of ordinary skill in the art can construct applicators that apply drugs to larger or smaller areas by changing the placement and number of openings. For example, therapeutic drugs for treating an injured or diseased area in a vessel and for combination with the disclosed applicator can include antiplatelets, antithrombins, and antiproliferatives. Examples of antiplatelets and antithrombins include sodium heparin, LMW heparin, hirudin, hirulog, argatroban, forskolin, vapirprost, prostacyclin, dextran, D-phe-pro-arg-chloromethylketone (synthetic antithrombin), dipyridamole, glycoprotein IIB/IIIa platelet membrane receptor antibody, recombinant hirudin, thrombin inhibitor (from Biogen) and 7E-3B (antiplatelet drug form Centocor). Examples of antiproliferatives include angiopeptin (somatostatin analogue from a French company: Ibsen), angiotensin convening enzyme inhibitors (Captopril (Squibb), Cilazapril (Hoffman-LaRoche) and Lisinopril (Merk)), calcium channel blockers (Nifedipine), colchicine, fibroblast growth factor (FGF) antagonists, fish oil (omega 3-fatty acid), low molecular weight heparin (Wyeth, Glycomed), histamine antagonists, lovastatin (inhibitor of HMG-CoA reductase, cholesterol lowering drug from Merk), methotrexate, monoclonal antibodies (to PDGF receptors, etc.), nitroprusside, phosphodiesterase inhibitors, prostacyclin analogues, prostaglandin inhibitor (Glaxo), seramin (PDGF antagonist(, serotonin blockers, steroids, thioprotease inhibitors, triazolopyrimidine (PDGF antagonist from Japanese company). While the foregoing therapeutic agents have been used to prevent or treat restenosis and thrombosis, they are provided by way of example and not meant to be limiting, as other therapeutic drags may be developed which are equally applicable for use with the present invention.

Figure 9:
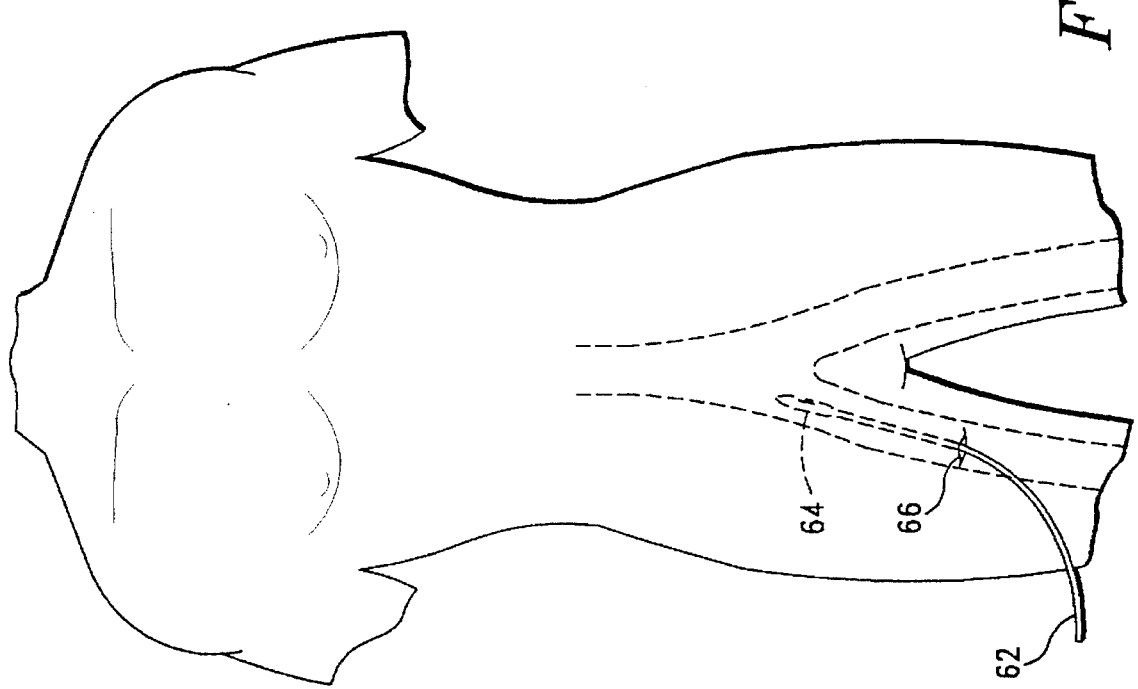
FIG. 9 illustrates the entry of a device constructed in accordance with the invention into a blood vessel.

FIG. 9 illustrates the entry of a device constructed in accordance with the invention into a biological conduit, showing a catheter 62 containing a device in accordance with the invention being inserted into a blood vessel 64 through an incision 66.

Figure 10:
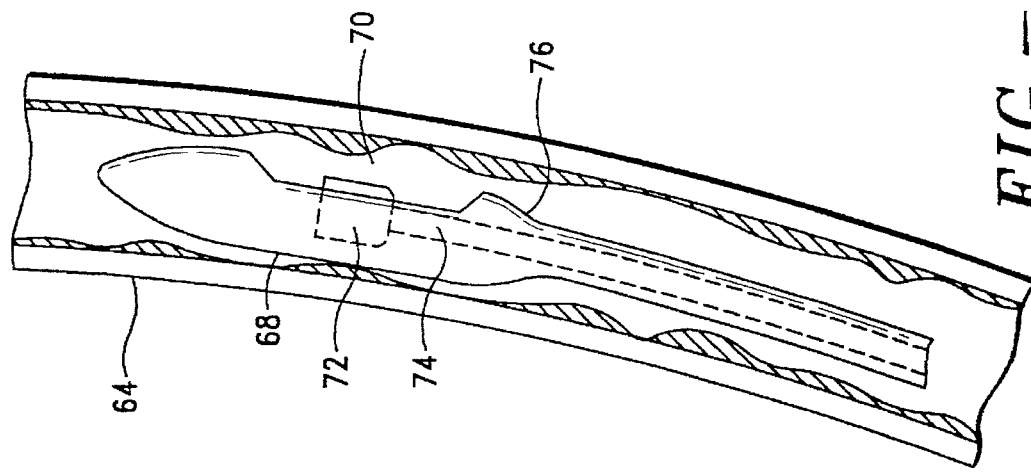
FIG. 10 illustrates the positioning of a device constructed in accordance with the invention within a blood vessel in conjunction with an atherectomy catheter.

With reference to FIG. 10, a device 70 constructed in accordance with the invention is positioned within a blood vessel 64. Applicator 72 attached to cable 74 is disposed within the housing 68 of a catheter 76.

Figure 2:
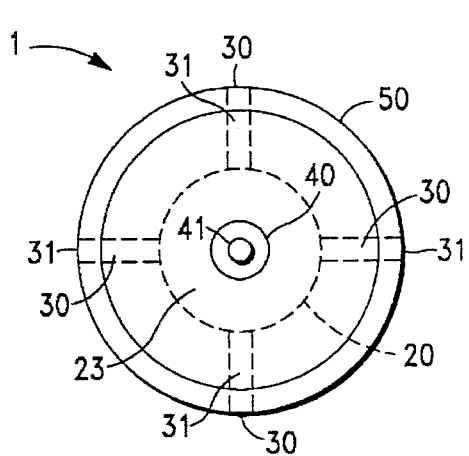
FIG. 2 is an end view and the applicator of FIG. 2.

FIG. 2 shows the relative positions of the drug delivery paths 30 with respect to a plane perpendicular to the central axis of the cutting applicator 1.

Figure 3:
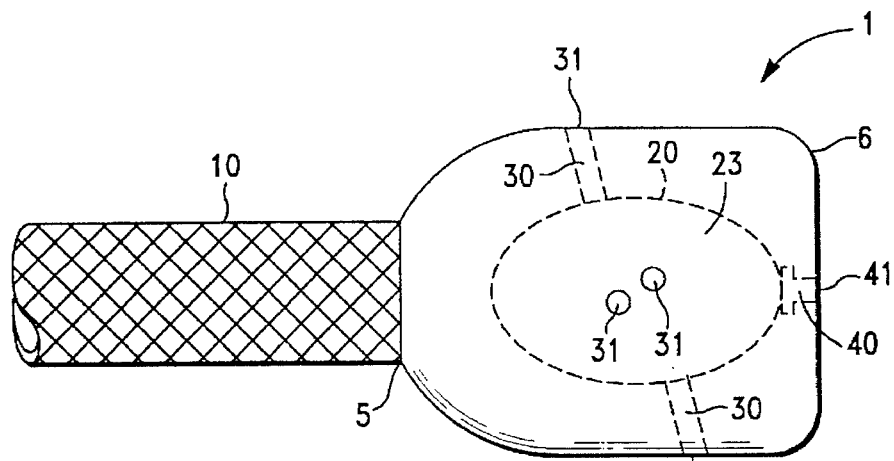
FIG. 3 is a side view of a non-cutting embodiment of the present invention.

FIG. 3 describes an embodiment wherein applicator 1 does not perform any cutting action. With respect to FIG. 3 is shown a medicament applicator 1 having a proximal end 5, a distal end 6, a medicament reservoir 20, delivery paths 30, exterior openings 31, and sealing plug 40. Applicator 1 is attached to drive cable 10 which is attached to a motor drive (not shown). As in the previous embodiment, the drug to be delivered can be loaded into reservoir 20 through port 41 and sealed in place by plug 40. In this preferred embodiment, reservoir 20 contains an absorbent material that will retain the absorbed drug until applicator 1 is rotated at speed high enough to overcome the absorptive forces. Once applicator 1 is positioned, drug is released when it is rotated at a suitable speed.

Figure 4:
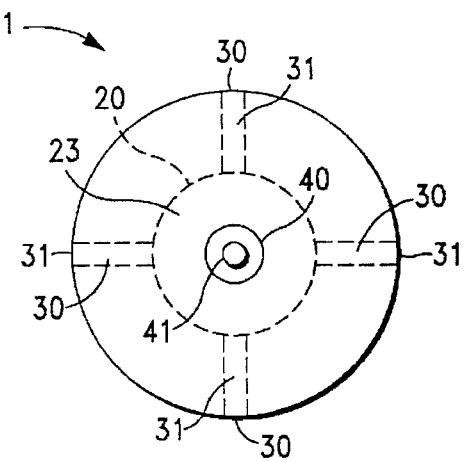
FIG. 4 is an end view of the applicator of FIG. 3.

FIG. 4 shows the relative positions of the drug delivery paths 30 with respect to a plane perpendicular to the central axis of the cutting applicator 1.

Figure 5:
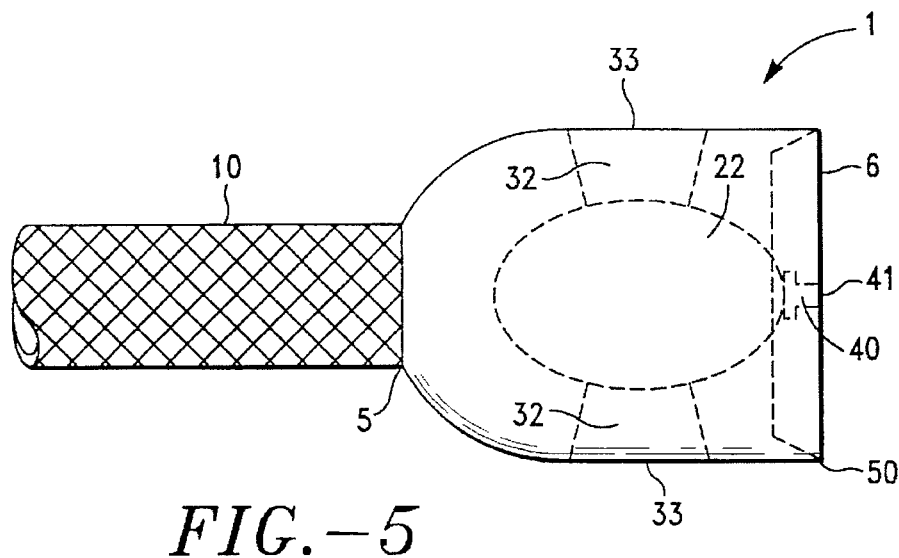
FIG. 5 is another embodiment of a cutting applicator in accordance with the present invention.
Figure 6:
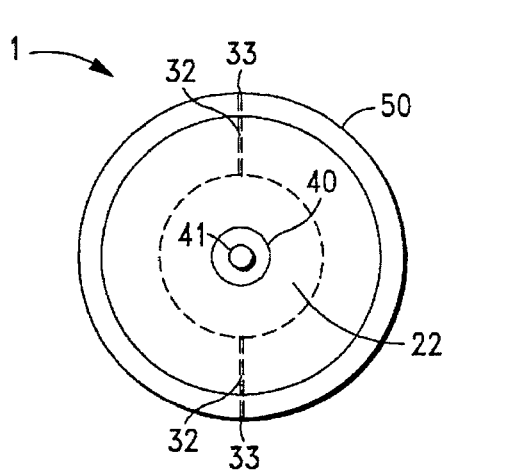
FIG. 6 is an end view and the applicator of FIG. 5.
Figure 8:
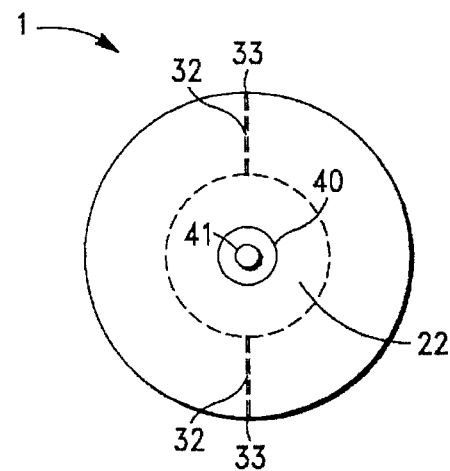
FIG. 8 is an end view and the applicator of FIG. 7.

FIG. 5 shows an embodiment of applicator 1 wherein the drug reservoir is devoid of any absorbent material and escape of the drug is controlled by the diameter of the capillary-like drag delivery paths 32 and the speed of applicator 1. The term "capillary-like" is used herein to describe the ordinary attraction between liquids and solids wherein a capillary bore will spontaneously fill when contacted with liquid and will not empty under ordinary gravitational forces. In the particular embodiment, the drug delivery paths 32 are slits of capillary dimensions. Slits 32 communicate with the surface via surface openings 33 and are wide enough to apply drug to a broader area than when a bore and a hole of capillary dimensions are used. As in the previous embodiment, the drug to be delivered can be loaded into the reservoir 22 when the device is manufactured through port 41 and sealed in place by plug 40 or alternatively, prepared just prior to treatment and injected into reservoir 31 through sealing plug 40 by means of a hypodermic syringe and needle. FIG. 6 shows the capillary nature of slits 33 more clearly. One skilled in the art can construct differently sized capillary conduits for the delivery of distinct amounts of drug at a desired rotational speed.

Figure 7:
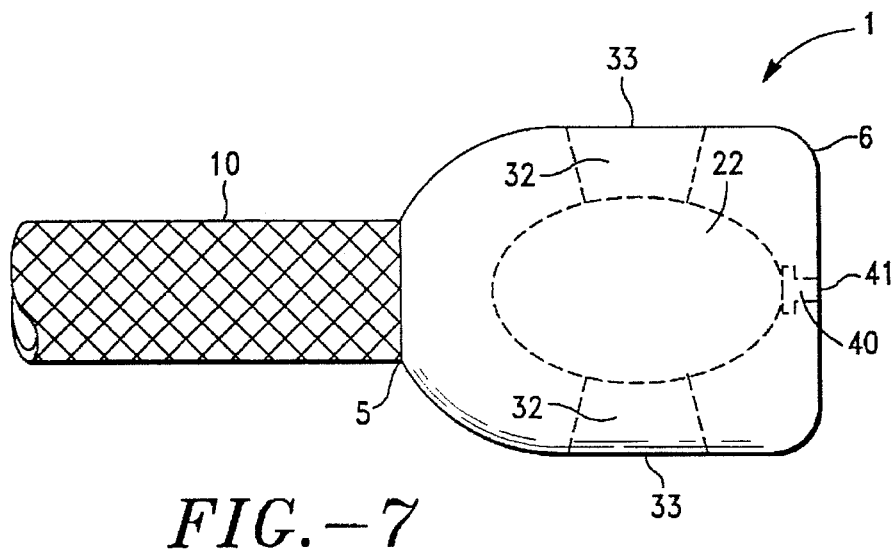
FIG. 7 is a non-cutting embodiment of the applicator in accordance with the present invention.

FIG. 7 describes another embodiment wherein the applicator 1 does not perform any cutting action. With respect to FIG. 6 is shown a medicament applicator 1 having proximal end 5, distal end 6, medicament reservoir 22, delivery paths 32, exterior openings 33, and sealing plug 40. Applicator 1 is attached to drive cable 10 at proximal end 5 which is attached to a motor drive (not shown). The drug to be delivered can be loaded into reservoir 22 through port 41 and sealed in place by plug 40. Drug reservoir 22 is devoid of any absorbent material and delivery of the drug is controlled by the diameter of the capillary-like drug delivery path 32 and the speed of rotation of applicator 1. In this specific embodiment, drug delivery paths 32 are slits of capillary dimensions. Delivery paths 32 communicate with the surface of applicator 1 via surface openings 33 and are wide enough to apply drug to a broader area than would be possible if a single bore and hole of capillary dimensions were used.

The foregoing detailed descriptions have described preferred embodiments of the drug delivery applicator of the instant invention and are to be understood to be illustrative only and not limiting of the disclosed invention. Particularly, the specific details of the drug delivery path and the construction of the reservoir can be varied to obtain different delivery rates and area of coverage and still be within the scope of the disclosed invention. Thus, the invention is to be limited only by the claims set forth below.

What is claimed is:

1. A device for the application of medicaments to a biological conduit, comprising:

a rotatable and axially translatable applicator, the applicator including:

an outer surface;

a distal end and a proximal end;

an interior reservoir for containing a medicament;

at least one delivery path connecting the interior reservoir to the surface of the applicator; and a drive cable attached to the proximal end of said applicator for imparting and translational motion to the applicator, whereby the medicament contained in the reservoir is deliverable to the biological conduit when the applicator is rotated.

2. The device of claim 1 wherein the biological conduit is a blood vessel.

3. The device of claim 2 wherein the blood vessel is a coronary blood vessel.

4. The device of claim 1 wherein the delivery path is of capillary dimensions.

5. The device of claim 4 wherein the biological conduit is a blood vessel.

6. The device of claim 5 wherein the blood vessel is a coronary blood vessel.

7. A device for the removal of tissue from, and the application of medicaments to, a biological conduit, comprising:

a rotatable and axially translatable applicator, the applicator including:

an outer surface;

a distal end and a proximal end;

an interior reservoir for containing a medicament;

at least one delivery path connecting the interior reservoir to the surface of the applicator; and a drive cable attached to the proximal end of said applicator for imparting rotational and translational motion to the applicator, whereby the medicament contained in the reservoir is deliverable to the biological conduit when the applicator is rotated.

8. The device of claim 7 wherein the biological conduit is a blood vessel.

9. The device of claim 8 wherein the blood vessel is a coronary blood vessel.

10. The device of claim 7 wherein the delivery path is of capillary dimensions.

11. The device of claim 10 wherein the biological conduit is a blood vessel.

12. The device of claim 11 wherein the blood vessel is a coronary blood vessel.

13. A method for localized application of medicaments within a biological conduit, the method comprising the steps of:

providing a device that includes:

a rotatable and axially translatable applicator, the applicator including an outer surface;

a proximal end;

a distal end;

an interior medicament containing reservoir;

at least one delivery path connecting the interior medicament reservoir to the surface of the applicator; and a drive cable attached to the proximal end of said applicator for imparting rotational motion to said applicator, inserting the device in the biological conduit so that the applicator is adjacent to the treatment area; and rotating the applicator at a speed sufficient to force the contained medicament to the surface of the applicator and onto the surface of the biological conduit, whereby the medicament contained in the reservoir is delivered to the biological conduit.

14. The method of claim 13 wherein the biological conduit is a blood vessel.

15. The method of claim 14 wherein the blood vessel is a coronary blood vessel.

16. The method of claim 13 wherein the delivery path is of capillary dimensions.

17. The method of claim 16 where the biological conduit is a blood vessel.

18. The method of claim 17 where the blood vessel is a coronary blood vessel.

19. A method for surgically intervening within a biological conduit, the method comprising the steps of:
   providing a device that includes:
      a rotatable and axially translatable applicator, the applicator including
      an outer surface;
      a proximal end;
      a distal end;
      a cutting means at the distal end of the applicator;
      an interior medicament containing reservoir;
      at least one delivery path connecting the interior medicament reservoir to the surface of the applicator; and
      a drive cable attached to the proximal end of said applicator for imparting rotational and translational motion to said applicator,
   inserting the device in the biological conduit so that the applicator is adjacent to the treatment area; and rotating the applicator at a speed sufficient to force the contained medicament to the surface of the applicator and onto the surface of the biological conduit,
   whereby the medicament contained in the reservoir is delivered to the biological conduit.

20. The method of claim 19 wherein the biological conduit is a blood vessel.

21. The method of claim 20 wherein the blood vessel is a coronary blood vessel.

22. The method of claim 19 wherein the delivery path is of capillary dimensions.

23. The method of claim 22 wherein the delivery path is of capillary dimensions.

24. The method of claim 23 wherein the blood vessel is a coronary blood vessel.

* * * * *